US00PP37842P2

(12) United States Plant Patent
Masor

(10) Patent No.: US PP37,842 P2
(45) Date of Patent: Nov. 10, 2026

(54) ***CALIBRACHOA* PLANT NAMED 'WICAMARD27'**

(50) Latin Name: *Calibrachoa hybrida*
Varietal Denomination: WICAMARD27

(71) Applicant: Laura Lee Masor, Buda, TX (US)

(72) Inventor: Laura Lee Masor, Buda, TX (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 19/458,747

(22) Filed: Jan. 24, 2026

(51) Int. Cl.
*A01H 5/02* (2018.01)

(52) U.S. Cl.
USPC ..... Plt./413

(58) Field of Classification Search
USPC ..... Plt./413
CPC ..... A01H 6/821; A01H 5/02
See application file for complete search history.

*Primary Examiner* — Keith O. Robinson
(74) *Attorney, Agent, or Firm* — C. Anne Whealy

(57) ABSTRACT

A new and distinct *Calibrachoa* plant named 'WICAMARD27', characterized by its upright to outwardly spreading and mounding to trailing plant habit; moderately vigorous to vigorous growth habit; freely branching habit; dense and bushy appearance; early and freely flowering habit; iridescent double-type flowers that are lavender in color with a yellow-colored central star-shaped pattern; and excellent container and garden performance.

2 Drawing Sheets

Figure 1:
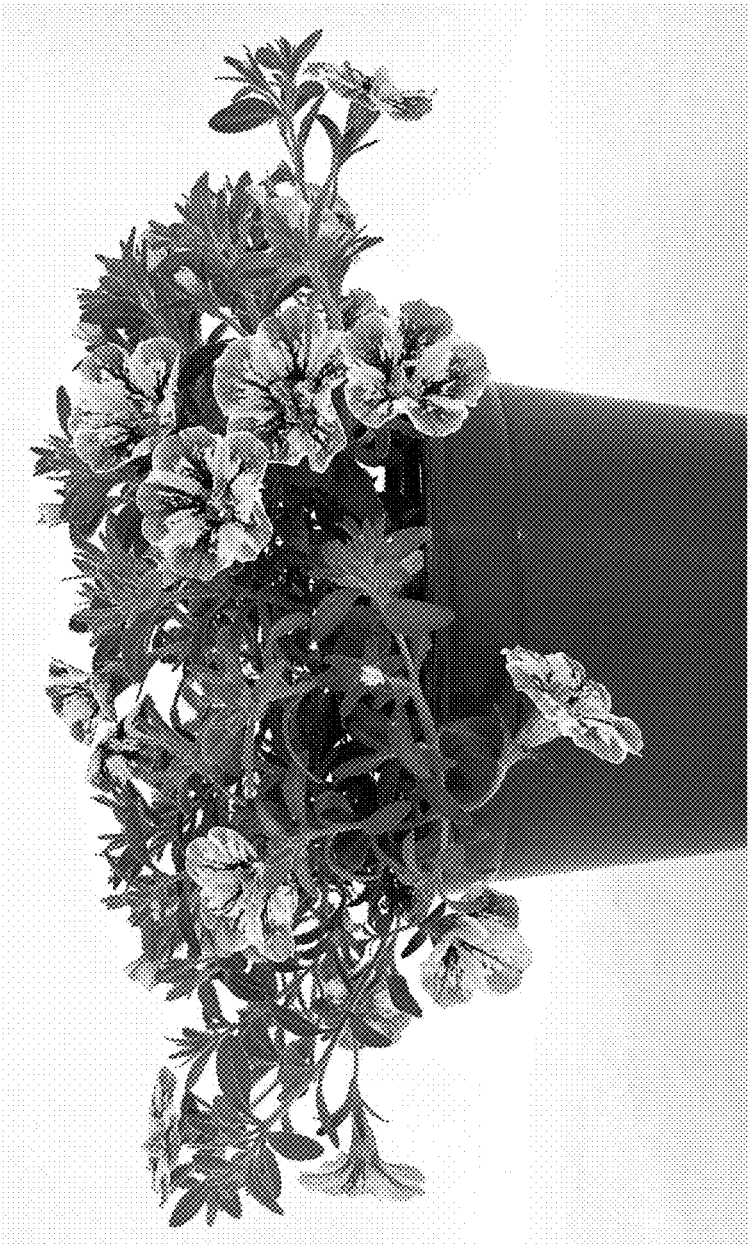

Botanical designation: *Calibrachoa hybrida.*
Cultivar denomination: 'WICAMARD27'.

BACKGROUND OF THE INVENTION

The present invention relates to a new and distinct cultivar of *Calibrachoa* plant, botanically known as *Calibrachoa hybrida* and hereinafter referred to by the name 'WICAMARD27'.

The new *Calibrachoa* plant is a product of a planned breeding program conducted by the Inventor in Buda, Texas. The objective of the breeding program is to create new uniform, freely-branching and freely-flowering *Calibrachoa* plants with semi-double type flowers with unique coloration and good container and garden performance.

The new *Calibrachoa* plant originated from a cross-pollination conducted by the Inventor in Buda, Texas on Oct. 20, 2022 of a proprietary seedling selection of *Calibrachoa hybrida* identified as code number CAL-01412-03, not patented, as the female, or seed, parent with a proprietary seedling selection of *Calibrachoa hybrida* identified as code number CAL-02065-02, not patented, as the male, or pollen, parent. The new *Calibrachoa* plant was discovered and selected by the Inventor as a single flowering plant within the progeny of the stated cross-pollination in a controlled greenhouse environment in Buda, Texas on Jun. 22, 2023.

Asexual reproduction of the new *Calibrachoa* plant by vegetative terminal cuttings in a controlled greenhouse environment in Buda, Texas since Jul. 31, 2023 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WICAMARD27'. These characteristics in combination distinguish 'WICAMARD27' as a new and distinct *Calibrachoa* plant:

1. Upright to outwardly spreading and mounding to trailing plant habit.
2. Moderately vigorous to vigorous growth habit.
3. Freely branching habit; dense and bushy appearance.
4. Early and freely flowering habit.
5. Semi-double type flowers that are lavender in color with a yellow-colored central star-shaped pattern.
6. Excellent container and garden performance.

Plants of the new *Calibrachoa* differ primarily from plants of the female parent selection in the following characteristics:

1. Plants of the new *Calibrachoa* are more freely branching than plants of the female parent selection.
2. Plants of the new *Calibrachoa* have smaller leaves than plants of the female parent selection.
3. Flowers of plants of the new *Calibrachoa* are semi-double types whereas flowers of plants of the female parent selection are double types.
4. Flowers of plants of the new *Calibrachoa* are lavender in color with a yellow-colored central star-shaped pattern whereas flowers of plants of the female parent selection are purple in color with white-colored marginal streaks.

Plants of the new *Calibrachoa* differ primarily from plants of the male parent selection, in the following characteristics:

1. Plants of the new *Calibrachoa* are more freely branching than plants of the male parent selection.

2. Flowers of plants of the new *Calibrachoa* are lavender in color with a yellow-colored central star-shaped pattern whereas flowers of plants of the male parent selection are pink and white bi-colored.

Plants of the new *Calibrachoa* can be compared to plants of the *Calibrachoa* sp. 'USCAL51505', disclosed in U.S. Plant Pat. No. 30,803. In side-by-side comparisons, plants of the new *Calibrachoa* differ primarily from plants of 'USCAL51505' in the following characteristics:

1. Plants of the new *Calibrachoa* are more compact than plants of 'USCAL51505'.
2. Plants of the new *Calibrachoa* are more freely branching plants of 'USCAL51505'.
3. Flowers of plants of the new *Calibrachoa* are lavender in color with a yellow-colored central star-shaped pattern whereas flowers of plants of 'USCAL51505' are pale yellow in color.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph on the first sheet (FIG. 1) is a side perspective view of a typical flowering plant of 'WICAMARD27' grown in a container.

Figure 2:
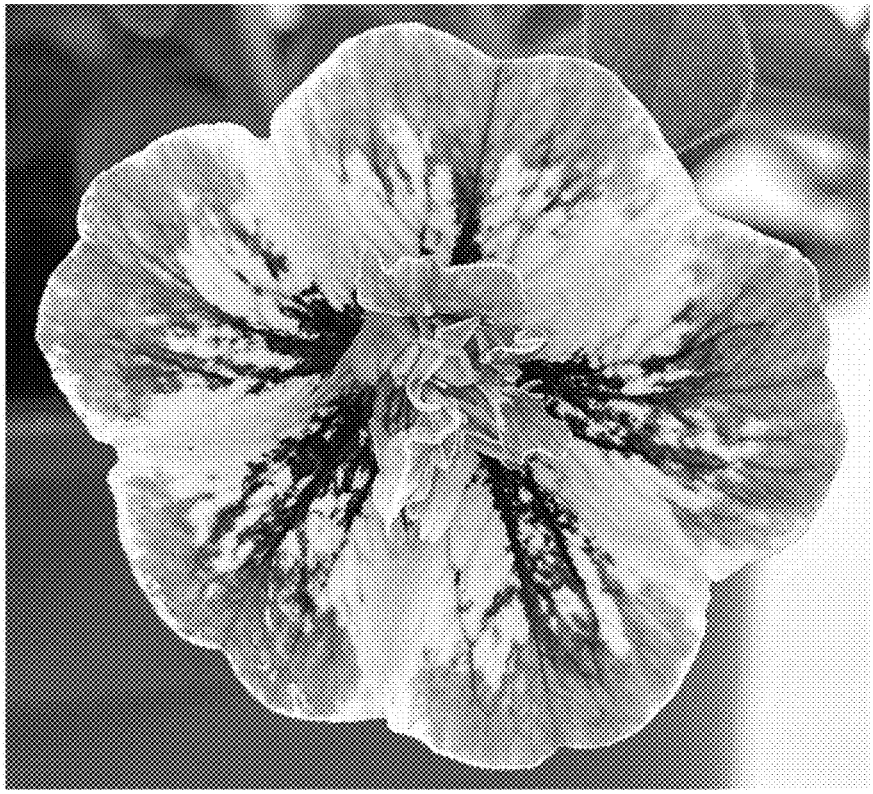

The photograph on the second sheet (FIG. 2) is a close-up view of a typical flower of 'WICAMARD27'.

DETAILED BOTANICAL DESCRIPTION

The aforementioned photographs and following observations and measurements describe plants grown during the late summer to early autumn in 740-ml containers in a glass-covered greenhouse in Loudon, New Hampshire and under cultural practices typical of commercial *Calibrachoa* production. During the production of the plants, day temperatures ranged from 18 °C to 20 °C and night temperatures ranged from 16 °C to 18 °C. Plants were pinched one time and were ten weeks from planting rooted young plants when the photographs and description were taken. In the following description, color references are made to The Royal Horticultural Society Colour Chart, 2015 Edition, except where general terms of ordinary dictionary significance are used.

Botanical classification: *Calibrachoa hybrida* 'WICAMARD27'.

Parentage:

*Female, or seed, parent*.—Proprietary seedling selection of *Calibrachoa hybrida* identified as code number CAL-01412-03, not patented.

*Male, or pollen, parent*.—Proprietary seedling selection of *Calibrachoa hybrida* identified as code number CAL-02065-02, not patented.

Propagation:

*Type*.—By vegetative terminal cuttings.

*Time to initiate roots, summer*.—About five to seven days at ambient temperatures about 28 °C.

*Time to initiate roots, winter*.—About seven to ten days at ambient temperatures about 20 °C.

*Time to produce a rooted plant, summer*.—About four to five weeks at ambient temperatures about 28 °C.

*Time to produce a rooted plant, winter*.—About five to six weeks at ambient temperatures about 20 °C.

*Root description*.—Thin, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright to outwardly spreading and mounding to eventually trailing plant habit; freely branching habit with about seven to nine primary lateral branches with secondary laterals developing potentially at every node, dense and bushy plant form; pinching enhances development of lateral branches; moderately vigorous to vigorous growth habit and rapid growth rate.

*Plant height*.—About 12 cm to 15 cm.

*Plant diameter*.—About 32 cm by 36 cm.

Lateral branch description:

*Length*.—About 18 to 21 cm.

*Diameter*.—About 4.5 mm.

*Internode length*.—About 7 mm to 9 mm.

*Strength*.—Moderately strong, flexible and sturdy; wiry.

*Aspect*.—Initially upright to horizontal to eventually trailing and decumbent.

*Texture and luster*.—Densely pubescent; pubescence, minute; matte to slightly glossy.

*Color, developing and developed*.—Close to between 144A and 146A.

Leaf description:

*Arrangement*.—Alternate, simple.

*Length*.—About 2.5 cm to 2.75 cm.

*Width*.—About 5 mm to 7 mm.

*Shape*.—Narrowly oblong to narrowly elliptic.

*Apex*.—Broadly acute.

*Base*.—Cuneate to attenuate.

*Margin*.—Entire.

*Texture and luster, upper and lower surfaces*.—Sparsely pubescent; margins, pubescent; pubescence, minute; matte to slightly glossy.

*Venation pattern*.—Pinnate.

*Color*.—Developing leaves, upper surface: Close to 146A. Developing leaves, lower surface: Close to 146A to 146B. Fully expanded leaves, upper surface: Close to 146A; venation, close to 146A. Fully expanded leaves, lower surface: Close to 146B; venation, close to 146B to 146C.

*Petioles*.—Length: About 4 mm to 5 mm. Diameter: About 1 mm. Strength: Moderately strong, flexible. Texture and luster, upper and lower surfaces: Sparsely pubescent; pubescence, minute; matte to slightly glossy. Color, upper and lower surfaces: Close to 146B.

Flower description:

*Flower type and flowering habit*.—Semi-double-type flowers arising from leaf axils; freely flowering habit with typically about 45 to 55 flowers and flower buds developing per plant at one time; flowers face upright to mostly outwardly.

*Fragrance*.—None detected.

*Natural flowering season*.—Depending on temperature, plants of the new *Calibrachoa* begin flowering about four to six weeks after planting; plants flower continuously from the spring though the summer until frost in New Hampshire.

*Flower longevity*.—Depending on temperature, flowers last about seven to ten days; flowers persistent.

*Flower buds, before showing petal color*.—Length: About 1.25 cm. Diameter: About 5 mm. Shape: Oblanceolate. Texture and luster: Moderately pubescent; pubescence, minute; matte. Color, sepals: Close to 144A.

*Flower diameter*.—About 3.5 cm to 3.7 cm.

*Flower length* (*height*).—About 2 cm to 2.4 cm.

*Flower tube length*.—About 1.5 cm.

*Flower tube diameter, proximally*.—About 2.25 mm.

*Corolla*.—Arrangement: Five petals in a single whorl with six to nine petaloids in one to two whorls; petaloids variable in size and shape. Petal lobe length: About 1.5 cm to 1.75 cm. Petal lobe width: About 1.5 cm. Petaloid lobe length (largest petaloids): About 1 cm. Petaloid lobe width (largest petaloids): About 1.1 cm. Petal and petaloid lobe shape: Spatulate to fan-shaped with cordate tendencies; petaloid shape irregular. Petal and petaloid lobe apex: Emarginate. Petal and petaloid lobe margin: Entire; moderately undulate. Petal and petaloid lobe texture and luster, upper surface: Smooth, glabrous; velvety; matte. Petal and petaloid lobe texture and luster, lower surface: Smooth, glabrous; matte. Tube texture and luster: Moderately pubescent; slightly glossy. Color, petals and petaloids: When opening and fully opened, upper surface: Close to 86C and N87C; central star shape, close to between 5A and 10A; narrow marginal edges, close to NN155D; venation, close to N92C. When opening and fully opened, lower surface: Close to 85A; dark violet-colored venation is visible from upper surface. Tube: Close to 85A to 85D.

*Calyx*.—Arrangement: One star-shaped calyx tube with five sepals fused towards the base and arranged in a single whorl; sepals flaring outwardly and reflexing towards the apex. Length: About 1.25 cm. Diameter: About 1 cm. Sepal length: About 1.25 cm. Sepal width: About 1 mm. Sepal shape: Narrowly lanceolate to acicular. Sepal apex: Acute. Sepal margin: Entire. Sepal texture and luster, upper and lower surfaces: Moderately pubescent; pubescence, minute; matte. Sepal color, upper and lower surfaces: Close to 146A.

*Peduncles*.—Length: About 1.5 cm to 2.25 cm. Diameter: About 1 mm. Angle: About 45° to 90° from stem axis. Strength: Moderately strong, flexible; wiry. Texture and luster: Sparsely pubescent; pubescence, minute; slightly glossy. Color: Close to between 144A and 146A.

*Reproductive organs*.—Stamens: Stamens are typically transformed into petaloids. Pistils: Quantity: One per flower. Pistil length: About 7 mm to 8 mm. Style length: About 5 mm to 6 mm. Style color: Close to 144B to 144C. Stigma diameter: Less than 1 mm. Stigma shape: Round. Stigma color: Close to 144B. Ovary color: Close to 144A.

*Seeds and fruits*.—To date, seed and fruit development have not been observed on plants of the new *Calibrachoa*.

Garden performance: Plants of the new Petunia have been observed to have excellent garden performance and have been observed to tolerate rain, wind and temperatures ranging from about 1° C. to about 35° C.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'WICAMARD27' as herein illustrated and described.

* * * * *